(12) United States Patent
Reiter et al.

(10) Patent No.: US 10,159,975 B2
(45) Date of Patent: Dec. 25, 2018

(54) MICROFLUIDIC DEVICE

(71) Applicant: STRATEC Consumables GmbH, Salzburg (AT)

(72) Inventors: Gottfried Reiter, Adnet (AT); Dario Borovic, Hallein (AT)

(73) Assignee: STRATEC CONSUMABLES GMBH, Anif (AT)

( * ) Notice: Subject to any disclaimer, the term of this patent is extended or adjusted under 35 U.S.C. 154(b) by 515 days.

(21) Appl. No.: 14/653,006

(22) PCT Filed: Feb. 13, 2014

(86) PCT No.: PCT/EP2014/052848
§ 371 (c)(1),
(2) Date: Jun. 17, 2015

(87) PCT Pub. No.: WO2014/139751
PCT Pub. Date: Sep. 18, 2014

(65) Prior Publication Data
US 2015/0328635 A1 Nov. 19, 2015

(30) Foreign Application Priority Data

Mar. 14, 2013 (EP) .................................... 13159238

(51) Int. Cl.
*B01L 3/00* (2006.01)
*G01N 3/08* (2006.01)
(Continued)

(52) U.S. Cl.
CPC ........ *B01L 3/502707* (2013.01); *B29C 65/02* (2013.01); *B29C 65/4895* (2013.01);
(Continued)

(58) Field of Classification Search
CPC ..... B29C 66/71; B29C 65/02; B29C 65/4895; B29C 65/7817; B29C 65/8253;
(Continued)

(56) References Cited

U.S. PATENT DOCUMENTS 6,465,757 B1 10/2002 Chen
6,972,490 B2 12/2005 Chang et al.
(Continued)

FOREIGN PATENT DOCUMENTS

EP 0997261 A1 5/2000
EP 1520685 A1 4/2005
(Continued)

OTHER PUBLICATIONS

Chia-Wen Tsao, et al., "Bonding of thermoplastic polymer microfluidics," Microfluidics and Nanofluidics, vol. 6, No. 1, XP019667827, (2009), pp. 1-16.
(Continued)

*Primary Examiner* — Samuel P Siefke
(74) *Attorney, Agent, or Firm* — 24IP Law Group; Timothy R DeWitt

(57) ABSTRACT

A microfluidic device includes a first substrate made of a first polymer material and a second substrate made of a second polymer material, the first and second substrates having respective bonding surfaces, at least one of the bonding surfaces having channel formations so that, when the bonding surfaces are bonded by surface deformation to one another, the bonded first and second substrates and the channel formations form at least part of a microfluidic channel network comprising a plurality of microfluidic channels, wherein one or more indicator pits, separate to the channel formations defining the microfluidic channel network, are formed in at least one of the bonding surfaces, so that surface deformation caused by the bonding process
(Continued)

causes a change of configuration of the one or more indicator pits.

10 Claims, 7 Drawing Sheets

(51) Int. Cl.
| | | |
|---|---|---|
| *B29C 65/48* | (2006.01) | |
| *B29C 65/82* | (2006.01) | |
| *B29C 65/00* | (2006.01) | |
| *B29C 65/02* | (2006.01) | |
| *G01B 11/16* | (2006.01) | |
| *G01B 11/22* | (2006.01) | |
| *B81C 1/00* | (2006.01) | |
| B29L 31/00 | (2006.01) | |
| B29C 65/78 | (2006.01) | |
| B29K 23/00 | (2006.01) | |

(52) U.S. Cl.
CPC ...... *B29C 65/8253* (2013.01); *B29C 66/1122* (2013.01); *B29C 66/53461* (2013.01); *B29C 66/54* (2013.01); *B29C 66/543* (2013.01); *B29C 66/97* (2013.01); *B81C 1/00119* (2013.01); *G01B 11/16* (2013.01); *G01B 11/22* (2013.01); *G01N 3/08* (2013.01); B01L 2200/12 (2013.01); B01L 2300/06 (2013.01); B01L 2300/0645 (2013.01); B01L 2300/0816 (2013.01); B01L 2300/0861 (2013.01); B01L 2300/0887 (2013.01); B01L 2300/12 (2013.01); B29C 65/7817 (2013.01); B29C 66/028 (2013.01); B29C 66/71 (2013.01); B29C 66/712 (2013.01); B29C 66/73365 (2013.01); B29C 66/9674 (2013.01); B29K 2023/38 (2013.01); B29L 2031/756 (2013.01); B81B 2201/058 (2013.01); B81C 2203/036 (2013.01); Y10T 156/10 (2015.01)

(58) Field of Classification Search
CPC ............... B29C 66/028; B29C 66/1122; B29C 66/53461; B29C 66/54; B29C 66/543; B29C 66/712; B29C 66/73365; B29C 66/9674; B29C 66/97; B29K 2023/06; B29K 2023/38; B29K 2025/06; B29K 2025/08; B29K 2033/12; B29K 2069/00; B29K 2077/00; B01L 2200/12; B01L 2300/06; B01L 2300/0645; B01L 2300/0816; B01L 2300/0861; B01L 2300/0887; B01L 2300/12; B01L 3/502707; B29L 2031/756; B81B 2201/058; B81C 1/00119; B81C 2203/036; G01B 11/16; G01B 11/22; G01N 3/08; Y10T 156/10
See application file for complete search history.

(56) References Cited

U.S. PATENT DOCUMENTS

| | | |
|---|---|---|
| 7,449,716 B2 | 11/2008 | Chen et al. |
| 2005/0067085 A1 | 3/2005 | Katayama |
| 2007/0141805 A1* | 6/2007 | Chang ............... B01L 3/502707 438/456 |
| 2009/0181228 A1* | 7/2009 | Gandhi ............. B01L 3/502707 428/213 |
| 2010/0163869 A1 | 7/2010 | Yang et al. |
| 2011/0162785 A1* | 7/2011 | Zhou ..................... B01F 5/0688 156/196 |
| 2016/0184820 A1* | 6/2016 | Reiter ............... B01L 3/502707 422/82.05 |

FOREIGN PATENT DOCUMENTS

| | | |
|---|---|---|
| JP | 2007-283677 A | 11/2007 |
| JP | 2009-83502 A | 4/2009 |
| JP | 2011-183589 A | 9/2011 |

OTHER PUBLICATIONS

Giuliano Bissacco, et al., "Precision manufacturing methods of inserts for injection molding of microfluidic systems," ASPE Spring Topical Meeting on Precision Macro/Nano Scale Polymer Based Component & Device Fabrication, ASME, 2005, 7 pages.
Laurie Brown, et al., "Fabrication and characterization of poly(methylmethacrylate) microfluidic devices bonded using surface modifications and solvents," The Royal Society of Chemistry 2006, Lab Chip, 2006, vol. 6, pp. 66-73.
Usama M. Attia, et al., "Micro-Injection Moulding of Polymer Microfluidic Devices," Microfluidics and Nanofluidics, vol. 7, No. 1, Jul. 2009, pp. 1-28.
International Search Report dated May 23, 2014 in PCT/EP2014/052848 filed Feb. 13, 2014.

* cited by examiner pre-bonding → after bonding
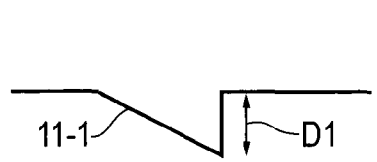
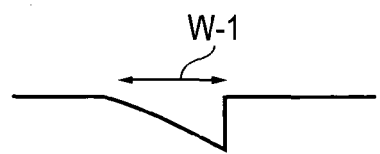
FIG. 7A  FIG. 7B
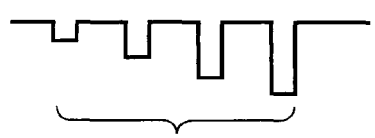
FIG. 8A  FIG. 8B
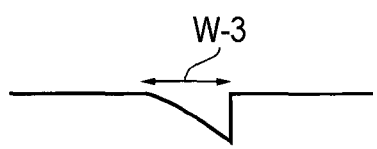
FIG. 9A  FIG. 9B
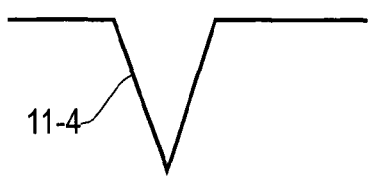
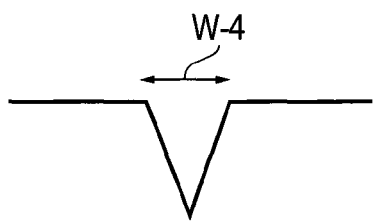
FIG. 10A  FIG. 10B
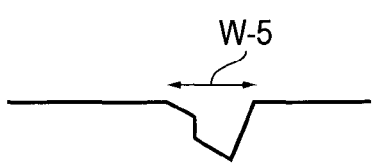
FIG. 11A  FIG. 11B

MICROFLUIDIC DEVICE

CROSS-REFERENCE TO RELATED APPLICATIONS

The present application is based on PCT filing PCT/EP2014/052848 filed Mar. 14, 2008, and claims priority to European Patent Application 13159238.8, filed in the European Patent Office on Mar. 14, 2013, the entire contents of each of which being incorporated herein by reference.

BACKGROUND

Field

The present disclosure relates to microfluidic devices and methods of manufacture and inspection of such devices.

Description of Related Art

The background description provided here is for the purpose of generally presenting the context of the disclosure. Work of the presently named inventors, to the extent that it is described in the background section, as well as aspects of the description which may not otherwise qualify as prior art at the time of filing, are neither expressly nor implicitly admitted as prior art against the present disclosure.

Microfluidic circuits are typically manufactured as planar structures from two substrates which are bonded together and arranged in a carrier. The carrier is sometimes referred to as a caddy. In the case of polymer substrates, thermal bonding and solvent vapour bonding are example bonding methods. In particular, thermal bonding has advantages for biological applications in that no contaminants are involved, for example in comparison to adhesive bonding. Microfluidic circuit elements, such as channels and mixing chambers, are formed at the interface between the substrates by surface structures in one or both of the substrates.

Thermal bonding and solvent vapour bonding rely on first softening one or both of the polymer surfaces to be bonded and then pressing the two surfaces together to induce some deformation. Although an amount of deformation is required to form a good bond, too much deformation will have a negative effect on the fine surface structure that forms the microfluidic channels and other microfluidic features of the device. On the other hand, if there is not enough deformation the bond is likely to be physically weak and potentially leaky. It is therefore necessary to bond in such a way that the deformation is enough, but not too much.

The amount of vertical compression that is caused by bonding can be measured by measuring the channel depth in the finished device structure, since the channel depth prior to bonding is known. The difference between the channel depth pre- and post-bonding is therefore a measure of the bonding-induced compression. A known destructive method to measure channel depth is to cut the bonded part at a channel and measure the depth of the channel at the section with a light microscope or a scanning electron microscope (SEM). There are non-destructive methods such as X-Ray tomography or optical methods available, but such equipment is expensive and in some instances are not particularly accurate.

SUMMARY

According to a first aspect of the present disclosure, there is provided a microfluidic device including: a first substrate made of a first polymer material and a second substrate made of a second polymer material, the first and second substrates having respective bonding surfaces, at least one of the bonding surfaces having channel formations so that, when the bonding surfaces are bonded by surface deformation to one another, the bonded first and second substrates and the channel formations form at least part of a microfluidic channel network including a plurality of microfluidic channels, wherein one or more indicator pits, separate to the channel formations defining the microfluidic channel network, are formed in at least one of the bonding surfaces, so that surface deformation caused by the bonding process causes a change of configuration of the one or more indicator pits.

This disclosure also provides a measurement instrument including: a microfluidic device as defined above; a processor configured to detect fluid measurement results from the microfluidic device; and a detector configured to compare the deformation of the one or more indicator pits with the pre-bonding configuration of the one or more indicator pits to detect the amount of compression that occurred during bonding in the manufacture of the microfluidic device; the processor being configured to adjust one or more parameters in detecting fluid measurement results from the microfluidic device according to the amount of compression detected by the detector.

This disclosure also provides a method of manufacturing a microfluidic device, the method including: providing first and second substrates made of respective first and second polymer materials, the first and second substrates having respective bonding surfaces, at least one of the bonding surfaces having channel formations so that, when the bonding surfaces are bonded by surface deformation to one another, the bonded first and second substrates and the channel formations form at least part of a microfluidic channel network comprising a plurality of microfluidic channels, in which one or more indicator pits, separate to the channel formations defining the microfluidic channel network, are formed in at least one of the bonding surfaces; softening at least one of the bonding surfaces in preparation for bonding to each other; and bonding by compression the bonding surfaces of the first and second substrate, the compression causing a change of configuration of the one or more indicator pits.

Further respective aspects and features are defined by the appended claims.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIGS. 7A-7B, 8A-8B, 9A-9B, 10A-10B and 11A-11B schematically illustrate alternative cross-sectional formations of indicator pits;

DETAILED DESCRIPTION

Figure 1:
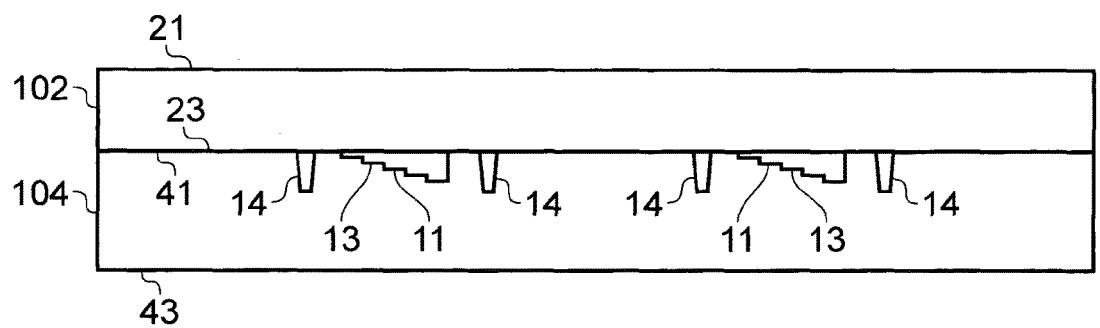
FIG. 1 is a schematic cross-section of a portion of a microfluidic device prior to bonding according to an embodiment of the present disclosure.

Referring now to the drawings, wherein like reference numerals designate identical or corresponding parts throughout the several views, FIG. 1 is a schematic cross-section of a portion of a microfluidic device according to an embodiment of the present disclosure. The device portion shown has two flat substrate layers. A substrate layer 102 is flat and unstructured over the illustrated portion (which is to say that the surface of the substrate layer 102 which contacts the other substrate layer is entirely flat over the illustrated portion), whereas a substrate layer 104 has an upper surface which is flat but also structured (which is to say that the layer is fundamentally flat, but has some structure or features impressed on it as surface depressions). The substrate layer 102 has a top surface 21 and a bottom surface 23. The substrate layer 104 has a top surface 41 and a bottom surface 43. Note that the terms "top" and "bottom" are used here merely to provide a clear reference to the diagrams including FIG. 1. The skilled person will understand that they do not imply or require any particular orientation of the assembled device in manufacture or in use.

The first and second substrate layers are made from respective first and second polymer materials. The first and second polymer materials may be the same or different, though in embodiments of the present disclosure the two materials are of the same "class" such as COP (defined below). In embodiments of the disclosure, the two materials are identical.

Suitable base polymers for the substrate layers include: polystyrene (PS), polyethylene (PE), cycloolefin polymer (COP), cycloolefin co-polymer (COC), styrene-acrylonitrile copolymer (SAN), polyamide (nylon), polycarbonate (PC), and polymethyl methacrylate (PMMA). Specific example plastics compounds are as follows. PS: BASF '158K' which is a high heat, clear material suitable for injection moulding; COP: Zeon Chemicals 'Zeonor 1060R' which is a clear, low water absorption material suitable for injection moulding; PMMA: Asahi Kasei 'Delpet 70NH' which is transparent and suitable for injection moulding; and HM671T 'PC Bayer MaterialScience AG 'Makrolon 2458' which is a medical grade, clear material suitable for injection moulding.

The structure in the upper surface 41 of the substrate layer 104 includes a number of microfluidic channels 14 which are illustrated as extending out of the plane of the drawing, so the drawing shows them in cross-section, as well as a number of multi-level indicator pits 11 which are arranged adjacent to but fluidically isolated from (that is, not in fluid communication with) the channels. As can be seen, the indicator pits are terraced into a plurality of levels, an example set of five such levels being shown in the figure, each level being formed by a respective plateau 13 that lies parallel to the substrate surface, the plateaux varying in respective depths between a minimum indicator pit depth and a maximum indicator pit depth. Note that in other embodiments, the formations illustrated as multi-level indicator pits could be implemented as wedge-shaped indicator pits, so that the depth of the indicator pit varies across the width of the indicator pit (the left to right direction as illustrated) smoothly and continuously rather than in steps, for example as a straight line function varying between a first (minimum indicator pit) depth and a second, different depth (a maximum indicator pit depth) at respective sides of the indicator pit. In other embodiments, a depth profile other than a straight line function could be used. It will also be appreciated that in a multi-level indicator pit, one or more of the features illustrated as plateaux in FIG. 1 may instead have a depth which varies across the width of the plateau feature, in other words forming a terraced level but one which has a varying depth across its width.

Here, the term "pit" signifies a hole formed in the surface of a substrate. The hole may have a stepped or otherwise varying depth. In some embodiments, the pits are blind holes, which is to say they are not through-holes to the other side of the substrate. In other embodiments a pit could be formed as a through-hole which is made blind by the bonding of a substrate to the other end of the hole.

Note also that the example indicator pits in FIG. 1 are shown schematically as having five levels, even though the device of FIG. 1 is already assembled. This is just to provide an initial explanation of the basic structure. In fact, the assembled device, in its finished form, may retain fewer of the levels which were initially formed in the substrate 104. The reason for this reduction in the number of levels during the manufacturing process will be discussed below. So for now, the five levels shown in FIG. 1 should be considered as schematically illustrating the state of the indicator pits 11 just before the assembly and bonding of the device.

To manufacture the device shown in FIG. 1, the lower surface 23 of the substrate layer 102 is to be bonded to the upper surface 41 of the substrate layer 104 so that when bonded they form at least part of a microfluidic channel network comprising the microfluidic channels 14. It will be understood that the network may extend to further interfaces between layers as may be provided for by providing a third substrate layer bonded to the first or second substrate layer, or indeed further substrate layers. Moreover, vertical holes may extend through the substrate layers to provide vertical fluid interconnections either to the outside or to further microfluidic features within the device. Note that the term "vertical" is used here merely for clarity of the description of this drawing, and as discussed before, the skilled person will appreciate that it does not place or imply any restrictions on the orientation of the device during manufacture or use.

The substrates are bonded by pressing them together after suitable softening of one or both of the contacting surfaces 23, 43. In embodiments, the surface which has the minority of (or none of, depending on the design) the microfluidic formations may be softened, to avoid distortion or a change in surface roughness of the microfluidic structures, but the other surface (or indeed both surfaces) could be softened. The process may be thermal bonding, in which case the softening is by heating. Alternatively, the process may be solvent vapour bonding, wherein softening is caused by exposure of one or both of the surfaces to a solvent vapour. Of course, solvent vapour bonding may also be associated with some heating (for example, to an elevated temperature which is below the glass transition temperature Tg of the material). There are also other softening techniques which may be used, instead of or in addition to the techniques already described. These include one or more of: plasma activation, ultraviolet activation, liquid solvent activation. All of these techniques can be considered to serve the same purpose: softening at least the surface of the material (possibly to a depth of just a few μm), for example by reducing the glass transition temperature Tg of the material. Other methods of softening may also (or instead) be used.

The pressing together of the two surfaces by compression induces some deformation as a result of the softening. Indeed, a certain amount of deformation is required for the bonding to be effective. If there is not enough deformation, the bond (and seal) between the two substrates is likely to be too weak (and potentially leaky). On the other hand, if there is too much deformation, then the fine structure of the microfluidic channel network is likely to be compromised. To measure the amount of deformation during bonding, the indicator pits are shaped and dimensioned such that, if the desired amount of deformation takes place for good bonding, then some but not all of the levels (that is, at least one shallowest level) of the indicator pits disappear, as an example of a change of configuration of the indicator pits. The number of levels being retained in the bonded product thus becomes an indicator of whether good bonding has taken place.

In the case of a wedge-shaped or similar indicator pit structure, the distance remaining (after bonding) between reference features (for example, distal edges) of the formations can provide such an indication of a change of configuration. Specific examples of such measurements will be discussed below.

Figures 2A, 2B, 2C:
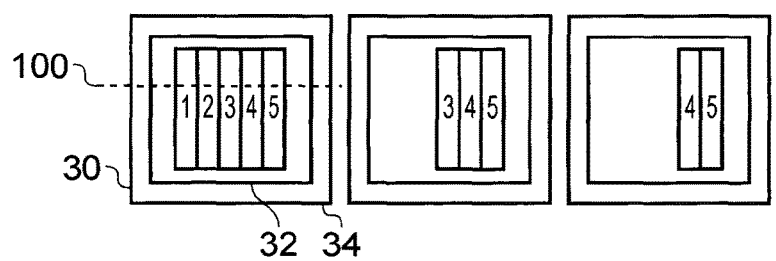
FIGS. 2A, 2B and 2C are schematic plan views of an example 5-level indicator pit before bonding and after bonding with lesser and greater amounts of compression respectively.

FIGS. 2A, 2B and 2C are schematic plan views of one of the example five-level indicator pits of FIG. 1.

FIG. 2A shows the indicator pit structure or configuration before bonding, or in other words, in the form in which the indicator pit is manufactured into the substrate 104. As mentioned, the view shown in FIG. 2A is a plan view, for example looking down onto the substrate 104 from the direction in which substrate 102 will be applied to form the device of FIG. 1. The cross-section shown in FIG. 1 may therefore be considered as a view across a plane 100 shown in FIG. 2A. Five levels of the multi-level indicator pit are shown in FIG. 2A, and are numbered as levels 1 . . . 5. Level 1 is the shallowest level, corresponding to the level drawn to the left hand side of an indicator pit 11 in FIG. 1. Level 5 is the deepest level, corresponding to the level drawn to the right hand side of an indicator pit 11 in FIG. 1.

An optional frame formation 30, bounded by edges 32 and 34, is illustrated in FIGS. 2A-2C. The frame is not shown in FIG. 1, but could of course be present (in which case it would be formed between the pits 11 and the channels 14). The frame could be a square or rectangular channel formation, not in fluid communication with the channels 14, used for alignment purposes. In embodiments, its depth could be the same as (or greater than) that of the deepest portion of the pits 11, so that the frame remains visible as long as a part of the pit structure remains visible. The frame can be useful in identifying and locating the pit structure during an optical or other examination of the device. The other embodiments in the present description may optionally include such a frame. Note that the frame does not have to form a closed loop around the pits; various other formations could be used, such as one or plural marker formations disposed with respect to the pits, in order to fulfil the basic function of assisting in finding the location of the pits during examination of the device.

FIGS. 2B and 2C are plan views in the same orientation as that of FIG. 2A, and illustrate the indicator pit structure or configuration, having been changed in response to the bonding process, with lesser and greater amounts of deformation and change of configuration having been induced by the compression respectively. FIG. 2B illustrates the situation where bonding has deformed the substrate to obliterate the first and second shallowest indicator pit levels 1, 2, so that the indicator pit levels 3, 4 and 5 remain. This is deemed to be an example of good bonding. FIG. 2C illustrates the situation where bonding has deformed the substrate to obliterate the first, second and third shallowest indicator pit levels 1, 2, 3, so that indicator pit levels 4 and 5 remain. This is deemed to be an example of bad bonding in that too much deformation has taken place.

Note that the indicator pit levels are used in this way to provide an observable or measurable indication as to how much deformation has taken place during the bonding process. The particular levels used in the indicator pits 11 may be selected so that the amount of deformation which is considered (for example, from empirical, possibly destructive, testing of other samples) to correspond to a "good" bond (enough deformation to provide a strong bond, but not so much as to deform the active channel and other formations) may correspond to the obliteration of approximately half of the indicator pit levels. This choice of an approximate half-way point for illustrating a desirable bond strength gives the potential for an indication of a weak or insufficient bond (more than half, but not all, of the indicator pit levels remain) or an excessively deformed bond (more than half, but not all, of the indicator pit levels have been obliterated). The use of multiple levels allows for an indication of the amount by which an actual bond deformation differs from a desired bond deformation, so as to allow for calibration and correction of the bonding process.

In one example, five steps or levels are provide, each with 500 nm height difference so that the depths of the steps relative to the substrate surface to be bonded are as follows: 1st step −500 nm, 2nd step −1000 nm, 3rd step −1500 nm, 4th step −2000 nm, 5th step −2500 nm (here, the negative sign indicates that the levels are below the surface of the substrate). This step height used in this example was determined by previous experiments which showed that for good thermal bonding with a particular example polymer such as Zeonor 1060R a compression or deformation of 2-3 μm is reasonable, though in some examples (such as ones in which compensation is required for large burrs at the channel edges) a deformation of up to 5 μm may be appropriate. If a different polymer requires a different deformation to achieve a strong bond, then differently arranged steps could be used. In a stepped arrangement, as few as two levels may be used in some embodiments, so as to provide a "correct/incorrect" indication of the bonding deformation. In other embodiments, more than two levels may be used, or (as discussed below) a varying level may be used.

Note that the deformation, measured in linear units (such as μm) indicates the distance (measured perpendicular to the substrate surface) by which the surface of the softened substrate is forced to retreat from its initial (pre-bonding) position by virtue of the other substrate being pressed onto it. Note however that in some respects this definition represents a perfect case, in which the whole of the bonding surfaces are in intimate contact before any bonding takes place. In reality, there may be burrs protruding from the microstructured surface, for example at the edges of the channel formations, which burrs can inhibit such intimate contact before bonding. During thermal bonding such burrs are depressed.

As well as adapting the step heights to the deformation appropriate to different materials to be bonded, the step heights can also be adapted to various bonding conditions. In some cases strong bonding conditions are required to achieve a seal that is tight at high pressure and in such case greater bonding deformations can be tolerated or even required. In other cases, weaker bonding conditions can be accepted, for example for low pressure applications or capillary filling applications. It is also noted that different bonding methods (with the same materials) may have different desirable bond deformations. For example, using a certain example polymer for both substrates, a thermal bond may be considered appropriately strong with a compression or deformation of 2 μm, whereas with the same polymer, a solvent vapour bond may be considered appropriately strong with a compression or deformation of 1 μm.

A manufactured microfluidic device part can therefore be tested after bonding and passed or rejected (failed) based on comparing the number of levels in the indicator pits with the pre-manufacture number of levels, to assess the amount of compression that has occurred during the bonding. A pass is based on the compression being at or above a lower limit (2 out of 5 in this example) and at or below an upper limit (3 out of 5 in this example) defined by numbers of levels remaining in the indicator pits after bonding. This test can be manual, for example a visual inspection with the naked eye or through an optical microscope, or can be automated by incorporating some suitable image processing to an optical microscope which might be a conventional microscope or a confocal microscope. The test can be carried out immediately after bonding, so that rejection of faulty parts can take place on the intermediate (newly bonded but otherwise unprepared) product, which is much earlier in the manufacturing process than would be the case if the fault was first detected through leak testing which would require complete assembly of the device. In any case, leak testing is itself time consuming and may be a purely destructive test for a microfluidic device, since the fluid used for the leak test may contaminate the device and render it unusable.

In addition, the multi-level indicator pits may be used during bonding to control the bonding process, by providing active monitoring of the obliteration or change in configuration of of levels in one or more example indicator pits 11 during the compression process and controlling the bonding process according to the monitoring. For example, a force pressing together the parts during bonding is continued or increased until the threshold minimum number of steps (indicative of an acceptably strong bond) has disappeared and then is removed (or maintained at that level) so as to avoid continuing the deformation too far and obliterating more than the threshold number of steps.

As schematically illustrated in FIG. 1, in embodiments of the present disclosure the indicator pits, before bonding, have a greatest indicator pit depth (the depth of the level 5 in the example of FIG. 2A) less than the channel depth of the microfluidic channels before bonding. This is consistent with the role of the indicator pits which is to measure an amount of deformation which should occur during bonding, which deformation should be too small to have a significant deforming effect on the microfluidic channels. Of course the indicator pits could be made deeper than the channels, but the extra depth would in practice serve no useful function, since the channels would be completely obliterated before the deepest indicator pit level. The greatest indicator pit depth is thus preferably considerably smaller than the channel depth, for example a factor of 2-50 times less than the channel depth, bearing in mind that generally the bonding-induced compression deformation should not substantially deform the channel structure. Purely as an example, for a 500 μm deep channel and an expected deformation of 5 μm, the greatest pit depth could be (say) 10 μm.

As illustrated in FIG. 1, in some embodiments it is convenient to form the indicator pits in the surface which contains the majority (or, in some embodiments, all) of the structuring for the microfluidic network. However, indicator pits could be formed in the other bonding surface as well as or instead. So, in the example of FIG. 1, the indicator pits 11 are shown as being formed in the surface 41, but they could instead (or as well) be formed in the surface 23. In embodiments of the disclosure, indicator pits 11 are formed in one surface so as to be opposed to a flat (unstructured) portion of the other bonding surface. In other words, in embodiments of the disclosure, an indicator pit is not formed in one surface so as to opposed to a indicator pit formed in the other surface. This arrangement can avoid confusion in the observed results.

Since a main purpose of the indicator pits is to assess integrity of the bond for the microfluidic device features, it is beneficial to arrange the indicator pits close to microfluidic device features—in particular those which are likely to be most critical for the function of the microfluidic device. Relevant features of the microfluidic channels include: a channel itself, a junction between microfluidic channels; an inlet of a microfluidic channel from a port, reservoir or chamber; an outlet of a microfluidic channel from a port, reservoir or chamber; a bend in a microfluidic channel; and a portion of a microfluidic channel where an electrode is arranged. For example, the closest part of an indicator pit to an adjacent channel may be arranged to lie between a minimum of 1-10 channel widths away from a portion of an adjacent microfluidic channel and a maximum of 2-20 channel widths away. Moreover, in some embodiments, indicator pits 11 are arranged in pairs on either side of a particular channel, in particular equidistant from that channel.

In some embodiments, the substrate 102 may be an unstructured layer (save for vias or ports) with both the microfluidic structure and the indicator pit structure being formed in the upper surface of the first substrate. In other embodiments, the lower surface of the second substrate may be structured in addition to the upper surface of the first substrate, with the structure in both surfaces contributing to the formation of the microfluidic channel network.

Accordingly, FIGS. 1 and 2A-2C provide an example of a microfluidic device comprising: a first substrate 102 made of a first polymer material and a second substrate 104 made of a second polymer material, the first and second substrates having respective bonding surfaces 23, 41, at least one of the bonding surfaces 41 having channel formations 14 so that, when the bonding surfaces are bonded by surface deformation to one another, the bonded first and second substrates and the channel formations form at least part of a microfluidic channel network comprising a plurality of microfluidic channels, wherein one or more indicator pits 11, separate to the channel formations 14 defining the microfluidic channel network, are formed in at least one 41 of the bonding surfaces, so that surface deformation caused by the bonding process causes a change of configuration of the one or more indicator pits.

Figure 3:
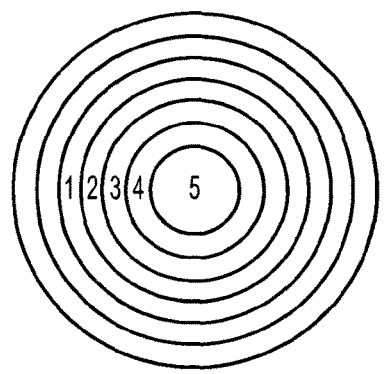
FIG. 3 schematically shows an alternative indicator pit shape.

FIG. 3 shows an alternative indicator pit shape. In the embodiment described above, the plateaux are rectangular and lie in parallel terraces. However, in FIG. 3, the plateaux are annular and concentric, in the manner of seating in an amphitheatre.

Other shapes for the terracing could be envisaged, for example, oval, semi-circular or otherwise arranged in arcuate or curved portions. Arbitrary shapes and non-geometric shapes are also possible.

Independent of the shape of the plateaux, the terrace levels may be equally spaced in height, for example by a height difference between 200 and 700 nanometers, or may be unequally spaced in height relative to each other and relative to the substrate surface from which they are recessed. For example, the shallowest, i.e. first, level may be relatively larger than the subsequent levels, such as, if a compression of at least a minimum threshold depth is needed for adequate bonding, then the shallowest level can be recessed by this minimum threshold depth. The plateaux may be smooth to provide good reflection. This may be desired to assist optical assessment of the plateaux, for example with an autofocus apparatus. In embodiments, a matte surface may be used because in the bonded state the matte surface will disappear and the plateaux will become invisible, so there is a clear difference between "original" and "compressed" plateaux. Also, it is convenient to focus an optical instrument onto a matte surface.

In particular, in autofocus inspection arrangements where high numerical aperture optical microscopy/scanning or confocal microscopy/scanning is used, the indicator pits 11 may form additional structures which can help or support the autofocus arrangement. The indicator pits 11 can be used for this purpose, for example by providing high contrast structures which are recognisable by image processing algorithms, so potentially reducing the time taken for an autofocus apparatus to complete its operation and/or to increase the accuracy of the autofocus inspection.

Figure 12:
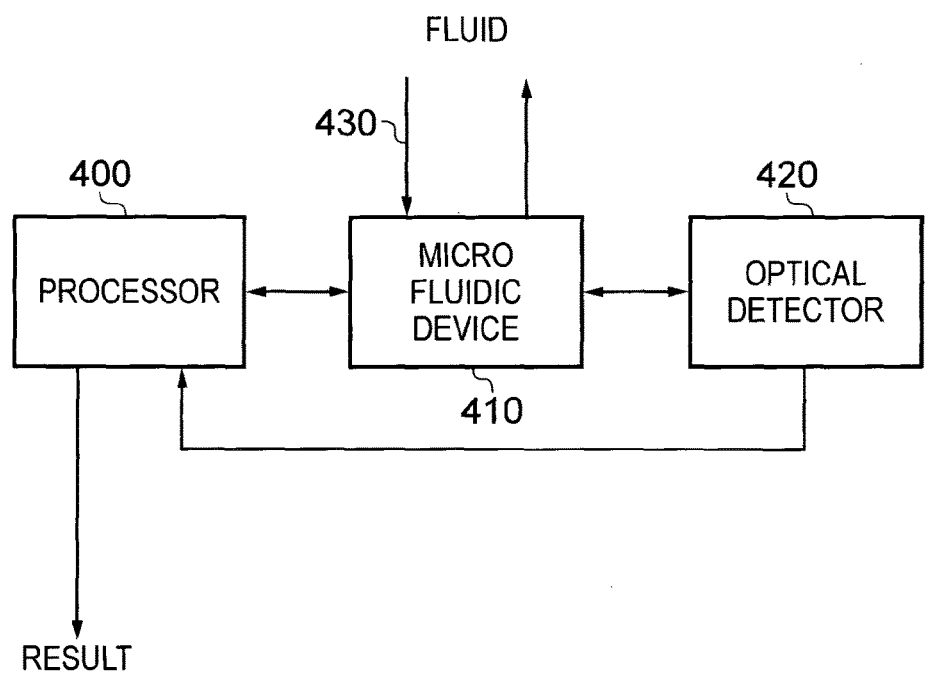
FIG. 12 schematically illustrates a measurement instrument.

For some applications in which the device is incorporated into an instrument such as a fluid testing instrument, then as well as the potential use of the indicator pits for acceptance testing during manufacture of the device, it could be beneficial to use these indicator pit structures in the final instrument for adapting the instrument to the device. An example instrument is shown schematically in FIG. 12, comprising a processor 400, a microfluidic device 410 as described in the present specification and an optical detector 420. The processor 400 is configured to detect fluid measurement results from the microfluidic device by controlling the microfluidic device and interprets its output as an output result. The microfluidic device performs a fluid test or detection on an input fluid 430. The optical detector 420 detects the surface deformation (compression) that occurred during bonding (in the manufacturing process) by optical detection of the indicator pits and sends a signal to the processor 400 indicative of the detected deformation. The processor 400 adjusts one or more parameters in detecting fluid measurement results from the microfluidic device according to the amount of compression detected by the optical detector.

For example, if the measurement to be made by the instrument is sensitive to the channel depth, the instrument could deduce the channel depth by evaluating the additional structures (the indicator pits 11, for example) instead of the manufacturer providing measurement information together with the device or chip, since the channel depth will be approximated by the channel depth prior to bonding less the vertical compression that was caused by the bonding, which is evidenced by the number of remaining levels of the indicator pit.

In embodiments, during manufacturing the deformation can be detected by optical detection and can for instance be written "onto" the device in the form of human readable text or machine readable code, for instance by generating a barcode (either direct writing onto the chip using a laser, ink-jet printing or printing a barcode onto a label which is attached to the chip) or writing the data onto an RFID (radio frequency identification) chip, attached to the device.

Figure 4:
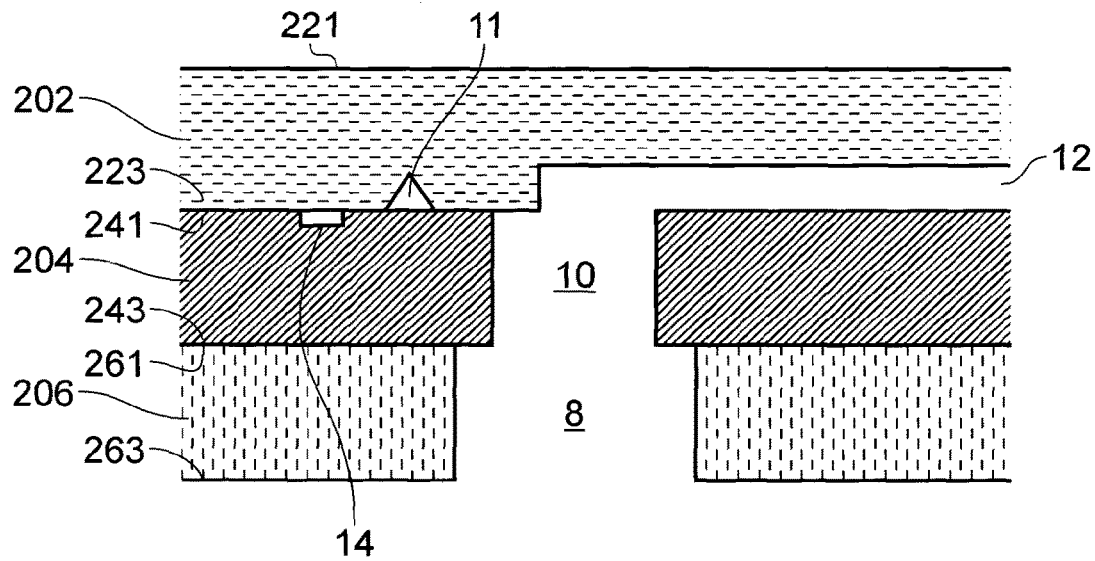
FIG. 4 is a schematic cross-section of a portion of an example microfluidic device.

FIG. 4 is a schematic cross-section of a portion of an example microfluidic device 201.

The illustrated portion shows first, second and third substrate layers 202, 204 and 206, each made of a plastics material such as a polymer, in particular one of the polymers listed below in the section describing an injection moulding process. The first layer 202 has a top surface 221 and a bottom surface 223. The second layer 204 has a top surface 241 and bottom surface 243. The third layer 206 has a top surface 261 and bottom surface 263. Similar comments to those made in respect of FIG. 1 apply here with regard to the orientations "top", "bottom" and "vertical".

The bottom surface 223 of the first layer 202 is bonded to the top surface 241 of the second layer 204, for example by a thermal bonding or solvent vapour bonding process suitable for bonding the polymer materials used for the layers. A laterally extending microfluidic channel 12 is illustrated at the interface 223/241 between the first and second layers 202, 204 by surface structure in one or both of the first and second layers 202, 204 (although in the example used in the illustration, the surface structure is solely in the first layer 202). Another example channel 14 is illustrated which is formed by surface structure in the second layer 204. Vertically extending through-holes or vias 8 and 10 are formed in the second and third layers 204 and 206 which are in fluid communication with the microfluidic channel 12. As illustrated, the through-hole 10 in the second layer 204 need not exactly correspond dimensionally to the through hole 8 in the third layer 206. The through-hole 10 in the second layer acts as a conduit for fluid communication between the channel 12 and the via 8. The purpose of the via 8 is to provide external access for the supply or removal of fluid, (liquid or gas), from the microfluidic circuit formed at the interface 223/241. In implementations of the design, the precise form and dimensions of the features 8 and 10 may be varied both in absolute terms and relative to one another. For example, the through-hole 10 could in fact be implemented as a micro-channel or at least a hole which is much narrower than the via 8 in third layer 206, so long as it is in fluid communication with the lateral microfluidic channel 12, or other microfluidic circuit feature in the plane of the interface 223/241.

One or more indicator pits 11 may be used to assist (as described in the present specification) with bonding the device, particularly (though not exclusively) as regards the interface between the substrate layers 202 and 204. In the example shown, given that more macroscopic (that is, bigger) features such as the vias 8, 10 are provided between the substrate layers 204 and 206, the need for indicator pits is reduced because the correct operation of such features are less sensitive to errors in bonding. Note also that other bonding techniques (such as laser bonding) could be used between the substrate surfaces 243 and 261.

Figure 5B:
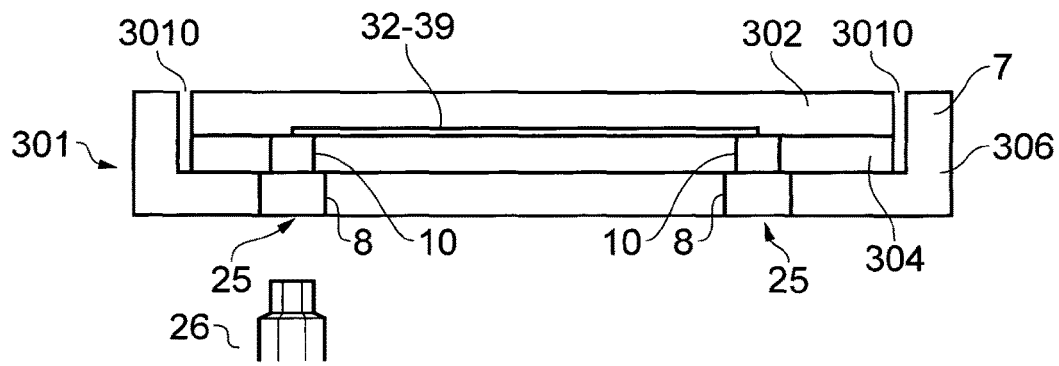
FIG. 5B is a schematic cross-section of the microfluidic device.
Figure 5A:
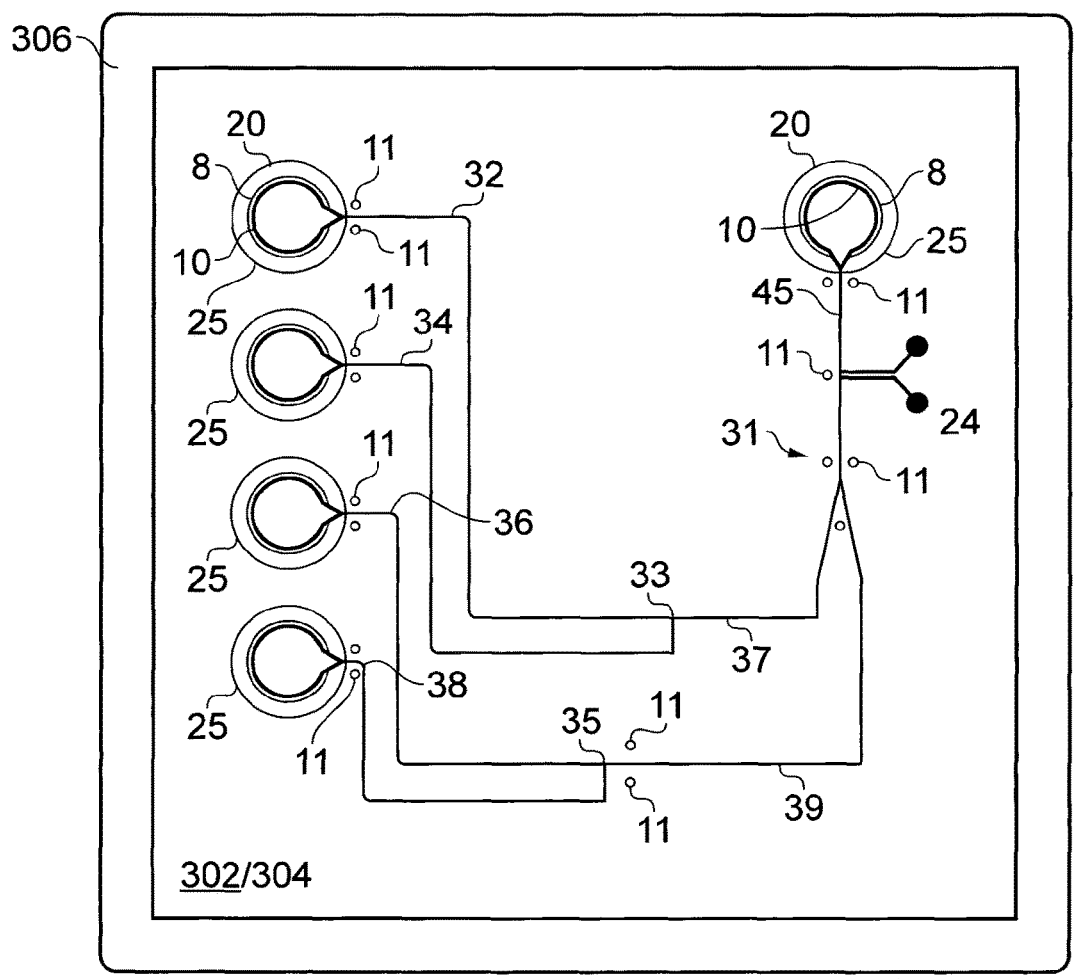
FIG. 5A is a schematic plan view of the whole example microfluidic device.

FIG. 5A is a schematic plan view of an example microfluidic device 301. FIG. 5B is a corresponding schematic cross-section, also showing a male Luer connector 26 shaped and dimensioned to engage into a female Luer connector formed by the holes 8 and 10. Substrate layers 302, 304, 306 are provided.

The third layer 306 is part of a carrier or caddy accommodating the microfluidic circuit formed by the bonded first and second layers 302 and 304. The carrier has side walls 7 which wrap around the edges of the first and second layers 302 and 304. A thermal expansion gap 3010 may be provided at the lateral edges of the substrate layers 302, 304, where thermal bonding is used between the substrate layer 304 and 306. In other arrangements, the carrier may be implemented using a laser absorbing material, using laser welding to combine the carrier 306 with the substrate layer 304.

A highly schematic microfluidic circuit is depicted, consisting of four female Luer connectors 25 as inlet ports, from which extend channels 32, 34, 36 and 38. Channels 32 and 34 join at a T-shaped droplet generator 33, and channels 36 and 38 join at a T-shaped droplet generator 35, the two merged channels 37 and 39 then in turn combining at a connection-shaped droplet generator 31 into a channel 45. An electrode portion 24 is also shown adjacent the channel 45 and serves, for example, to coalesce droplets of analyte and sample liquid passing along the channel. The channel 45 terminates in an outlet Luer port 25 with laser weld 20. It will be appreciated that in some implementations some of the inlet/outlet ports may be sealed with O-rings (or other gasket types) and others with continuous seam welds.

The indicator pits 11 are schematically illustrated in FIG. 5A with small squares (they are not shown in the particular cross-section of FIG. 5B). Only some of the indicator pits are indicated with reference numerals to avoid too many reference numerals and leading lines. As can be seen, pairs of indicator pits are arranged adjacent to the channel inlets of channels 32, 34, 36 and 38 as well as adjacent to the channel outlet of channel 45. The droplet generators 31, 33 and 35 are provided with three indicator pits as close as possible to the junction point. Moreover, the channel 45 near the electrode 24 is provided with three indicator pits either side of the electrode and either side of the channel portion closest to the electrode. Note that as described with reference to FIG. 4, it may be that indicator pits are appropriate as between the substrate layers 302, 304 but not necessarily between the substrate layer 304 and the carrier 306.

Figure 6:
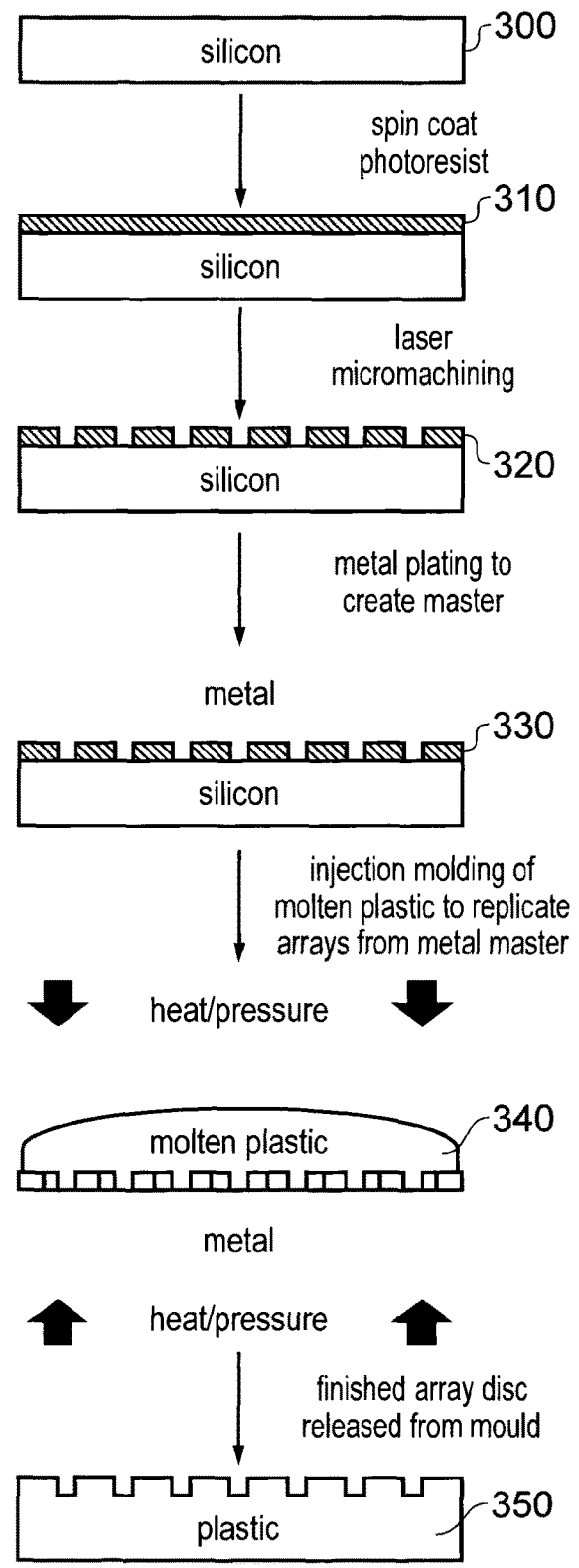
FIG. 6 schematically shows the principal steps in a substrate manufacturing process.

FIG. 6 shows the principal steps in a substrate manufacturing process using injection moulding.

The first part of the process is to manufacture a master.

A silicon or glass wafer 300 is spin coated with a photoresist 310. A laser or other suitable light source is then used to expose the photoresist to define a structure with high spatial resolution. The material to be exposed is transparent to the laser light used. However, in the focal volume of this highly focused laser beam a chemical or physical modification is created. Ultimately a selective solubility of the exposed area relative to the surrounding is achieved. In a developer bath, depending on the photosensitive material which is used, either the exposed or unexposed areas are removed. In other words, if the photoresist is such that exposure to the laser light leaves or renders it insoluble, and leaves or renders the unexposed material soluble, then the unexposed material is removed in the developer bath. For other photoresist materials the opposite could apply so that the developer bath removes the exposed material. Thus, almost any "2.5D" structures from a variety of photosensitive materials can be realized (for example SU-8 or the positive photoresist AZ9260 from AZ Electronic Materials are examples of suitable types of photoresist). Note that the expression "2.5D" is notation to indicate a three-dimensional structure which is limited by the fact that undercut formations cannot be implemented by this technique.

Alternative technologies for structuring the resist master are direct laser micromachining, e-beam lithography or mask based lithography processes. Laser write lithography can also be used with inorganic phase transition materials instead of the photoresist pushing the size resolution limit below the wavelength of the laser. Further details of applicable processes can be found in JP4274251B2 (equivalent to US2008231940A1) and JP 2625885 B2 (no English language equivalent). Further background documents relating to the fabrication process for microfluidic devices include: Bissacco et al, "Precision manufacturing methods of inserts for injection moulding of microfluidic systems", ASPE Spring Topical Meeting on Precision Macro/Nano Scale Polymer Based Component & Device Fabrication. ASME, 2005; Attia et al, "Micro-injection moulding of polymer microfluidic devices", Microfluidics and Nanofluidics, vol. 7, no. 1, Jul. 2009, pages 1-28; and Tsao et al, "Bonding of thermoplastic polymer microfluidics", Microfluidics and Nanofluidics, 2009, 6:1-16. All of these documents are hereby incorporated by reference.

Once the photoresist has been suitably structured and the exposed (or non-exposed, as the case may be) material removed to form a structured photoresist 320, a metal plating processing step is applied. Electroplating is used to deposit a nickel layer by electrolysis of nickel salt-containing aqueous solutions, so-called nickel electrolytes. Nickel electrolytes usually have nickel or nickel pellets as the anode. They serve the supply of metal ions. The process for the deposition of nickel has long been known and been highly optimized. Most nickel electrolytes to achieve an efficiency of >98%, which means that over 98% of the current supplied to be used for metal deposition. The remaining power is lost in unwanted electrolytic processes, such as hydrogen. The transcription of lithographically structured micro-features is strongly dependent on compliance with the correct parameters. Not only the continuous supply of additives, but also the metal ion content, the temperature and the pH value need to be maintained.

The result it a metal version 330 of the structure defined by the partially removed photoresist.

Direct milling into steel can be used as an alternative to silicon and photoresist in order to master such microstructures. Other methods, or other variations on the methods described above, are also possible, as described in the documents referenced below.

The master is then used in an injection moulding process to create the structured surfaces in polymer to incorporate both the structuring needed for the microfluidic channel network and also the multi-level indicator pits. In an injection moulding machine, polymers (shown generically as molten plastic 340 in FIG. 6) are plasticized in an injection unit and injected into a mould. The cavity of the mould determines the shape and surface texture of the finished part. The polymer materials need to be treated carefully to prevent oxidation or decomposition as a result of heat or sheer stresses. Heat and pressure are applied to press molten polymer onto the structured surface of the master. After a suitable filling, cooling and hardening time (noting that cooling and hardening take place together for thermoplastics), the heat and pressure are removed and the finished plastics structure 350 is ejected from the mould. The injection moulding process can then be repeated using the same master.

The cost of the master and the larger moulding tool it will form a part of represents a large part of the total necessary investment, so the process lends itself to high volumes. Simple tools enable economic viable prototyping from a threshold of a few thousand parts. Tools for production can be used up to make up to several million parts.

The injection moulded substrate can be further plasma treated to control the surfaces properties, for example to alter the glass transition temperature Tg or to change the surface tension (or contact angle, respectively).

Moreover, a coating can be applied to a whole surface or selectively applied to only some areas as desired. For example, sputtering, ink jet printing or aerosol jetting may be used to deposit a coating.

Finally, it is noted that the carrier may not include features requiring precision on the same small size scale as the layers which are used to form the planar microfluidic circuit elements. It will therefore be possible in some cases to manufacture the carrier using simpler or alternative methods.

FIGS. 7A-7B, 8A-8B, 9A-9B, 10A-10B and 11A-11B schematically illustrate alternative cross-sectional formations of indicator pits, and also ways in which the change of the configuration of the indicator pits after bonding can be used to detect the degree of compression or deformation of the surface.

The drawings are arranged as two columns of drawings. The left column, representing FIGS. 7A, 8A, 9A, 10A and 11A, provides a schematic and not-to-scale representation of a cross-section of an indicator pit structure in one substrate surface before the bonding process takes place.

The right column, representing FIGS. 7B, 8B, 9B, 10B and 11B, provides a schematic representation of the corresponding indicator pit structure after a bonding process with a notional bonding force or deformation has taken place. The drawings in the right column also schematically indicate a measurement by which the change of configuration of the indicator pits can be detected from the observable changes in the indicator pit structure.

FIG. 7A schematically illustrates a wedge shaped, or linearly varying depth, indicator pit 11-1. To detect the deformation after bonding in this case, the width w-1 of the resulting indicator pit can be detected. Note that the indicator pit 11-1 has an initial minimum depth of zero and an initial maximum depth of D1. The depth D1 (in common with the maximum depth in each of these embodiments) is less than the microfluidic channel depth.

FIG. 8A schematically illustrates a series or group of (in this example) four discrete adjacent indicator pits 11-2 of different single respective depths, each depth being less than the microfluidic channel depth. One or more such groups may be provided. During or after bonding, the deformation can be detected simply by counting the remaining (non-obliterated) indicator pits. Such an observation can be made during the bonding process so as to monitor the number of such pits remaining in a group, so that the bonding can be controlled according to the monitoring. In the example of FIG. 8B, two indicator pits remain after the bonding process. Note that although rectangular shaped pits (at least in lateral cross section) are shown, the pits could be, for example, cylindrical, cuboids, wedge shaped (V shaped in lateral cross section in at least one dimension), rounded cylinders (U shaped in lateral cross section), conical or the like.

FIG. 9A schematically illustrates a indicator pit 11-3 having (a) a non-zero minimum depth D2, and (b) a non-linear depth profile—in this example, a simple curve. Other non-linear profiles could be considered, for example having a flatter depth variation near to the required deformation amount, so as to give a finer indication, near to the correct depth, as to the amount of deformation applied. In FIG. 9B, the deformation is assessed by measuring the indicator pit width w-3.

FIG. 10A schematically illustrates a V-shaped indicator pit 11-4, and the deformation can be assessed by detecting the indicator pit width w-4 after bonding. Note that it may be that in a real situation, the side walls of the V-shaped indicator pit, when compressed, may bend or deviate towards the centre axis of the pit.

FIG. 11A schematically illustrates a stepped (staircase, multi-level) indicator pit, but in which there is a variation in depth within a levels and in the joining sections between each level. Again, the width w-5 can be used to assess the deformation after bonding.

Note that any combination of the above or other types of indicator pit could be used in the context of a single device or in the context of a single indicator pit formation. More than one example of any indicator pit configuration may be provided on a single substrate surface.

Figure 13:
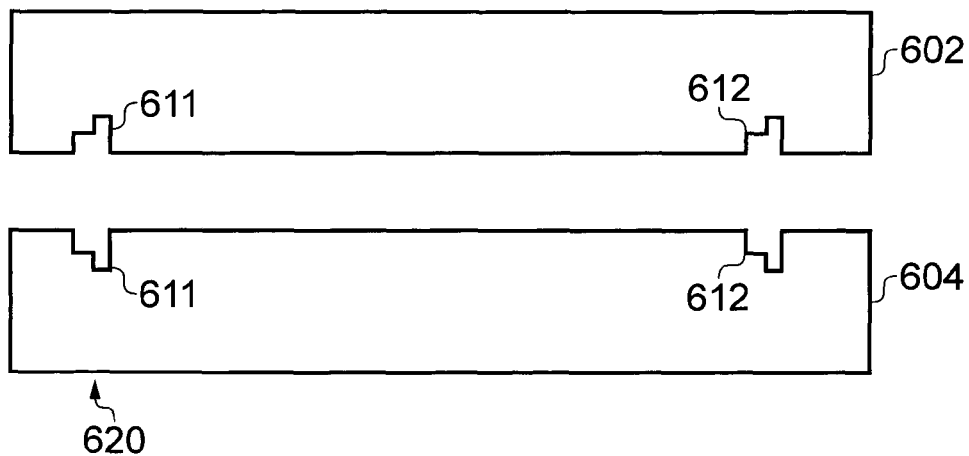
FIG. 13 schematically illustrates a use of indicator pits as alignment markers.

FIG. 13 schematically illustrates a use of indicator pits as alignment markers. In the example shown, two substrates 602, 604 to be bonded have one or more pairs 611, 612 of indicator pits at corresponding positions in the bonding surfaces of the two substrates. Here, "corresponding positions" is used to refer to the same position, in the bonded device so that the indicator pits in a pair should overlie one another in the bonded device. The indicator pits of these pairs can therefore be used during alignment of the substrates for bonding, for example by optically inspecting the pair of substrates in a direction perpendicular to the bonding surfaces (for example, in a direction 620) and laterally moving one or both substrates before bonding until the pairs of indicator pits are observed to overlie one another. A bonding force in the perpendicular direction 620 is then applied. Note that in respect of FIG. 13, other formations, such as other indicator pits and/or microfluidic formations may also be provided on one or both substrates, but are not shown (for clarity of the diagram) in FIG. 13. Note also that the change in configuration of an indicator pit disposed opposite another indicator pit (as in the pairs 611, 612) may be different to the change in configuration of an indicator pit 11 disposed opposite a flat portion of the other substrate.

Figure 14:
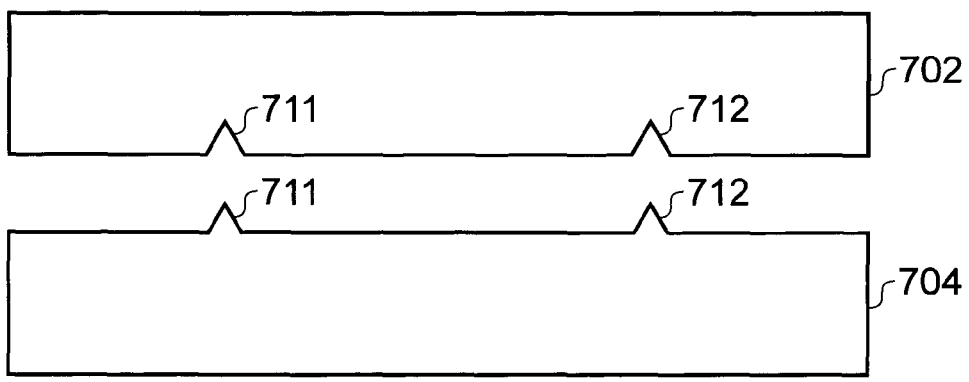
FIG. 14 schematically illustrates the use of complementary inter-engaging formations.

FIG. 14 schematically illustrates the use of complementary inter-engaging formations. These are not necessarily indicator pits but are formed by similar techniques and can provide a mechanical technique for assisting in alignment of substrates for bonding. In the example shown, two pairs 711, 712 of such formations are illustrated, but other numbers of pairs could be provided. Note that in respect of FIG. 14, other formations, such as indicator pits and/or microfluidic formations may also be provided on one or both substrates, but are not shown (for clarity of the diagram) in FIG. 14. The formations are provided at corresponding positions on the two substrates, as discussed above with reference to FIG. 13.

A pair of such formations includes one formation (shown in this example on a substrate 704) which at least partially protrudes from the substrate, and one formation (shown in this example on a substrate 702) which is at least partially indented into the substrate. In other embodiments, each formation of a pair may include indented and protruding portions, complementary to corresponding portions on the other formation of the pair. In embodiments, the protruding portion is smaller than the indented portion, to allow for the fact (as discussed above) that the two substrates are joined by compression bonding. The disappearance of the protruding portion into the corresponding indented portion can, in some embodiments, be optically observed to assist in the detection of an adequate bond depth.

In some embodiments, the formations may be chamfered or otherwise varied in size with their depth (or their protrusion) so as to act as a mechanical guide to direct the substrates towards the correctly aligned position.

Figure 15:
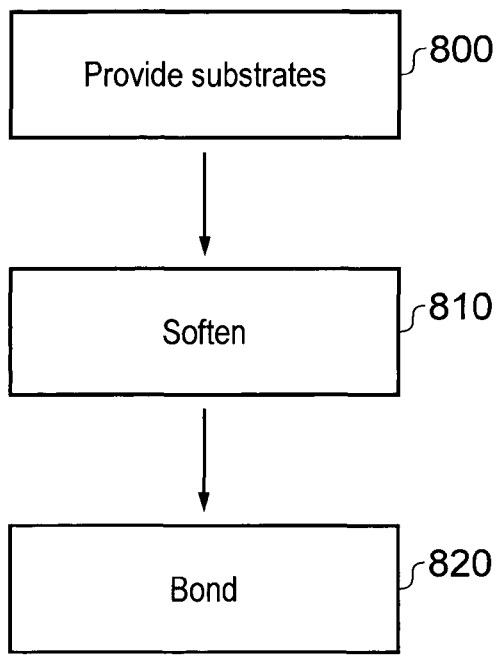
FIG. 15 is a schematic flowchart of a method of manufacture.

FIG. 15 is a schematic flowchart illustrating steps in a method of manufacturing a microfluidic device.

A step 800 comprises providing first and second substrates made of respective first and second polymer materials, the first and second substrates having respective bonding surfaces, at least one of the bonding surfaces having channel formations so that, when the bonding surfaces are bonded by surface deformation to one another, the bonded first and second substrates and the channel formations form at least part of a microfluidic channel network comprising a plurality of microfluidic channels, in which one or more indicator pits, separate to the channel formations defining the microfluidic channel network, are formed in at least one of the bonding surfaces.

A step 810 comprises softening at least one of the bonding surfaces in preparation for bonding to each other. For example, the softening can be heating (in which case thermal bonding is used) or by exposure to a solvent vapour (so that solvent vapour bonding is used).

A step 820 comprises bonding by compression the bonding surfaces of the first and second substrate, the compression causing a change of configuration of the one or more indicator pits.

Figure 16:
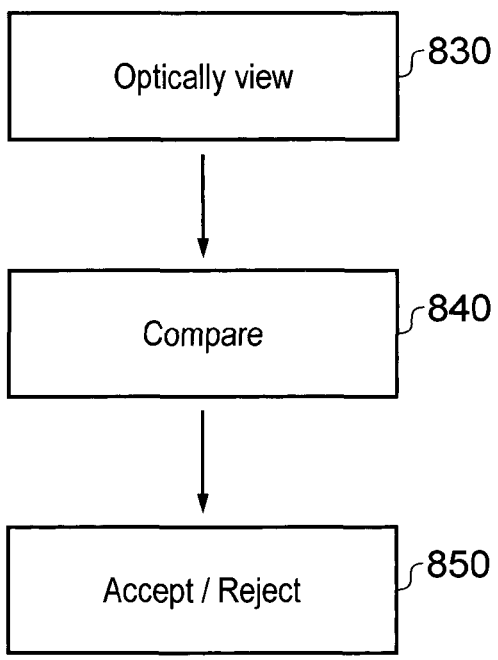
FIG. 16 is a schematic flow chart of an inspection method.

FIG. 16 is a schematic flow chart illustrating an inspection method for a microfluidic device manufactured according to the method of FIG. 15.

A step 830 comprises optically viewing the microfluidic device to inspect the deformation of the one or more indicator pits caused by the compression.

A step 840 comprises comparing the change of configuration of the one or more indicator pits with the pre-bonding configuration of the one or more indicator pits to detect the amount of compression that has occurred during the bonding.

A step 850 comprises accepting or rejecting the microfluidic device based on the detected amount of compression. In embodiments, acceptance of the device is based on the detected compression being at or above a lower limit and at or below an upper limit Especially by means of optical processes like grey scale lithography, the mastering of microstructures has become available for industrial application. This process gives sufficient design freedom to incorporate micro-features into channels, but also to create micro-structured indicator pits. The use of such technology is creating a one-time cost during mastering, but has minimal impact on the cost per product in large volume manufacturing. The improvement of the process control during the bonding process creates potential for more efficiency and lower per unit cost.

In summary, indicator pit structures such as multi-level indicator pit structures which are non-functional to the microfluidic circuit are provided at one or positions on the polymer parts in addition to the functional micro-structures in order to be able to adjust and/or monitor the polymer deformation during polymer bonding. During bonding the polymer parts are pressed together. The amount of deformation will depend on factors including the bonding pressure, the bonding temperature and the duration of the bonding. The type of activation and other process parameters may also influence the amount of deformation. The amount of deformation can be measured by comparing the deformation of the one or more indicator pits with the pre-bonding configuration of the one or more indicator pits to detect the amount of compression that has occurred during the bonding. The deformation can be measured in this way and used to adjust the bonding pressure during bonding, to check the bonding result after bonding and to quantify the compression of the micro-structures caused by the bonding process. The multilevel or other indicator pit structures can be incorporated together with microfluidic structure features during the preparation of the moulding/embossing/imprinting tools, or in processes such as hot embossing, laser machining or direct milling. Alternatively, the multilevel or other indicator pit structures can be introduced to the polymer parts after their initial manufacturing by milling, laser micromachining, etching or some other technique for selective removal of material.

Obviously, numerous modifications and variations of the present disclosure are possible in light of the above teachings. It is therefore to be understood that within the scope of the appended claims, the disclosure may be practiced otherwise than as specifically described herein.

Respective features of the present disclosure are defined by the following numbered paragraphs:

1. A microfluidic device including:
   a first substrate made of a first polymer material and a second substrate made of a second polymer material, the first and second substrates having respective bonding surfaces, at least one of the bonding surfaces having channel formations so that, when the bonding surfaces are bonded by surface deformation to one another, the bonded first and second substrates and the channel formations form at least part of a microfluidic channel network comprising a plurality of microfluidic channels,
   wherein one or more indicator pits, separate to the channel formations defining the microfluidic channel network, are formed in at least one of the bonding surfaces, so that surface deformation caused by the bonding process causes a change of configuration of the one or more indicator pits.

2. The device of paragraph 1, wherein the indicator pits are arranged adjacent to the microfluidic channels.

3. The device of paragraph 1 or 2, wherein one or more indicator pits are arranged adjacent to features of the microfluidic channels including at least one of: a junction between microfluidic channels; an inlet of a microfluidic channel from a port, reservoir or chamber; an outlet of a microfluidic channel from a port, reservoir or chamber; a bend in a microfluidic channel; and a portion of a microfluidic channel where an electrode is arranged.

4. The device of any one of paragraphs 1 to 3, wherein the indicator pits are fluidically isolated from the microfluidic channels.

5. The device of any one of paragraphs 1 to 4, wherein the indicator pits have a plurality of levels or a varying level between a minimum indicator pit depth and a maximum indicator pit depth, each formed by a plateau that lies parallel to the upper and lower surfaces.

6. The device of any one of paragraphs 1 to 5, wherein the microfluidic channels have a channel depth and the indicator pits have a maximum indicator pit depth less than the channel depth.

7. The device of any one of paragraphs 1 to 6, wherein the indicator pits are formed in that one of the first and second substrates which has the majority of the structures defining the microfluidic channels.

8. The device of any one of paragraphs 1 to 4, including one or more groups of adjacent indicator pits, each indicator pit in the group having a different respective depth.

9. The device of any one of the preceding paragraphs, in which the substrates are flat.

10. The device of any one of the preceding paragraphs, in which at least one pair of pits is provided at corresponding positions on the bonding surfaces of the first and second substrates so as to provide an alignment indicator for assembly of the device.

11. The device of any one of the preceding paragraphs, including one or more complementary inter-engaging formations on the respective bonding surfaces.

12. A method of manufacturing a microfluidic device, the method including:

providing first and second substrates made of respective first and second polymer materials, the first and second substrates having respective bonding surfaces, at least one of the bonding surfaces having channel formations so that, when the bonding surfaces are bonded by surface deformation to one another, the bonded first and second substrates and the channel formations form at least part of a microfluidic channel network including a plurality of microfluidic channels, in which one or more indicator pits, separate to the channel formations defining the microfluidic channel network, are formed in at least one of the bonding surfaces;

softening at least one of the bonding surfaces in preparation for bonding to each other; and bonding by compression the bonding surfaces of the first and second substrate, the compression causing a change of configuration of the one or more indicator pits.

13. The method of paragraph 12, in which the one or more indicator pits are multi-level indicator pits such that at least the shallowest one of the indicator pit levels of each indicator pit disappears under the compression.

14. The method of paragraph 13, wherein there are at least two levels in each multi-level indicator pit.

15. The method of paragraph 14, further including: monitoring the number of levels in the indicator pits during bonding; and controlling bonding according to the monitoring.

16. The method of paragraph 12, in which one or more groups of adjacent indicator pits are provided, each indicator pit in the group having a different respective depth.

17. The method of paragraph 16, further comprising: monitoring the number of indicator pits remaining in a group during bonding; and controlling bonding according to the monitoring.

18. The method of any one of paragraphs 12 to 17, wherein said softening and said bonding are selected from the list including:

said softening being heating and said bonding is thermal bonding; and said softening being exposure to a solvent vapour and said bonding being solvent vapour bonding.

19. An inspection method for a microfluidic device manufactured according to the method of any one of paragraphs 12 to 18, the method including:

optically viewing the microfluidic device to inspect the deformation of the one or more indicator pits caused by the compression;

comparing the change of configuration of the one or more indicator pits with the pre-bonding configuration of the one or more indicator pits to detect the amount of compression that has occurred during the bonding; and accepting or rejecting the microfluidic device based on the detected amount of compression.

20. The method of paragraph 19, wherein acceptance of the device is based on the detected compression being at or above a lower limit and at or below an upper limit.

21. A measurement instrument including:

a microfluidic device according to any one of paragraphs 1 to 11;

a processor configured to detect fluid measurement results from the microfluidic device; and a detector configured to compare the deformation of the one or more indicator pits with the pre-bonding configuration of the one or more indicator pits to detect the amount of compression that occurred during bonding in the manufacture of the microfluidic device;

the processor being configured to adjust one or more parameters in detecting fluid measurement results from the microfluidic device according to the amount of compression detected by the detector.

The invention claimed is:

1. A microfluidic device comprising:
a first substrate made of a first polymer material and a second substrate made of a second polymer material, the first and second substrates having respective bonding surfaces, at least one of the bonding surfaces having channel formations so that, when the bonding surfaces are bonded by surface deformation to one another, the bonded first and second substrates and the channel formations form at least part of a microfluidic channel network comprising a plurality of microfluidic channels,
wherein one or more indicator pits, separate to the channel formations defining the microfluidic channel network, are formed in at least one of the bonding surfaces, so that surface deformation caused by the bonding process causes a change of configuration of the one or more indicator pits,
at least one pair of pits is provided at corresponding positions on the bonding surfaces of each of the first and second substrates so as to provide an alignment indicator for assembly of the microfluidic device.

2. The device of claim 1, wherein the indicator pits are arranged adjacent to the microfluidic channels.

3. The device of claim 1, wherein one or more indicator pits are arranged adjacent to features of the microfluidic channels including at least one of: a junction between microfluidic channels; an inlet of a microfluidic channel from a port, reservoir or chamber; an outlet of a microfluidic channel from a port, reservoir or chamber; a bend in a microfluidic channel; and a portion of a microfluidic channel where an electrode is arranged.

4. The device of claim 1, wherein the indicator pits are fluidically isolated from the microfluidic channels.

5. The device of claim 1, wherein the indicator pits have a plurality of levels or a varying level between a minimum indicator pit depth and a maximum indicator pit depth, each of the plurality of levels being formed by a plateau that lies parallel to the upper and lower surfaces.

6. The device of claim 1, wherein the microfluidic channels have a channel depth and indicator pits have a maximum indicator pit depth less than the channel depth.

7. The device of claim 1, wherein the indicator pits are formed in that one of the first and second substrates which has the majority of the structures defining the microfluidic channels.

8. The device of claim 1, comprising one or more groups of adjacent indicator pits, each indicator pit in the group having a different respective depth.

9. The device of claim 1, in which the substrates are flat.

10. The device of claim 1, comprising one or more complementary inter-engaging formations on the respective bonding surfaces.

* * * * *